(12) United States Patent
Douglas et al.

(10) Patent No.: US 7,115,362 B2
(45) Date of Patent: Oct. 3, 2006

(54) ELECTROCHEMICAL TEST DEVICE AND RELATED METHODS

(75) Inventors: Joel S. Douglas, Groton, CT (US);
Jeffrey N. Roe, San Ramon, CA (US);
John H. Priest, Everett, WA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/287,522

(22) Filed: Nov. 23, 2005

(65) Prior Publication Data

US 2006/0088945 A1    Apr. 27, 2006

Related U.S. Application Data

(63) Continuation of application No. 10/224,875, filed on Aug. 21, 2002, now Pat. No. 7,018,848, which is a continuation of application No. 08/876,812, filed on Jun. 17, 1997, now Pat. No. 6,638,772.

(60) Provisional application No. 60/019,864, filed on Jun. 17, 1996.

(51) Int. Cl.
*C12Q 1/00* (2006.01)

(52) U.S. Cl. .................. 435/4; 204/400; 204/403; 435/287.1; 435/287.2; 435/817; 436/149; 436/169; 436/170; 436/524; 436/525; 436/805; 436/806

(58) Field of Classification Search .................. None
See application file for complete search history.

(56) References Cited

U.S. PATENT DOCUMENTS

| | | |
|---|---|---|
| 3,271,591 A | 9/1966 | Ovshinsky |
| 3,710,205 A | 1/1973 | Swanson |
| 3,983,076 A | 9/1976 | Rockstad et al. |
| 4,178,415 A | 12/1979 | Ovshinsky et al. |
| 4,217,374 A | 8/1980 | Ovshinsky et al. |
| 4,226,898 A | 10/1980 | Ovshinsky et al. |
| 4,634,514 A | 1/1987 | Nishizawa et al. |
| 4,994,167 A | 2/1991 | Shults et al. |
| 5,126,034 A | 6/1992 | Carter et al. |
| 5,137,827 A | 8/1992 | Mroczkowski et al. |

(Continued)

FOREIGN PATENT DOCUMENTS

EP    0 255 291 B1    2/1988

(Continued)

OTHER PUBLICATIONS

Yokoyama, K. et al., "Amperometric Glucose Sensor Using Silicon Oxide Deposited Gold Electrodes", ELECTROANALYSIS, May 1991, vol./Issue No. 3, pp. 469-475, VCH Publishers, Inc.

*Primary Examiner*—Christopher L. Chin
(74) *Attorney, Agent, or Firm*—Woodard, Emhardt, Moriarty McNett & Henry LLP

(57) ABSTRACT

An electrochemical test device is provided for determining the presence or concentration of an analyte in an aqueous fluid sample. The electrochemical test device includes a working electrode and a counter electrode made of an amorphous semiconductor material. The working electrode is overlaid with a reagent capable of reacting with an analyte to produce a measurable change in potential which can be correlated to the concentration of the analyte in the fluid sample. The test device optionally contains a reference electrode made of an amorphous semiconductor material having a reference material on the reference electrode. The test device electrodes can be constructed on a flexible film substrate, such as a polymeric film or a metal foil coated with a non-conductive coating.

19 Claims, 4 Drawing Sheets

U.S. PATENT DOCUMENTS

| | | |
|---|---|---|
| 5,143,694 A | 9/1992 | Schafer et al. |
| 5,174,963 A | 12/1992 | Fuller et al. |
| 5,277,870 A | 1/1994 | Fuller et al. |
| 5,296,194 A | 3/1994 | Igarashi |
| 5,312,762 A | 5/1994 | Guiseppi-Elie |
| 5,344,754 A | 9/1994 | Zweig |
| 5,391,250 A | 2/1995 | Cheney, II et al. |
| 5,395,504 A | 3/1995 | Saurer et al. |
| 5,413,690 A | 5/1995 | Kost |
| 5,437,999 A | 8/1995 | Diebold et al. |
| 5,468,606 A | 11/1995 | Bogart et al. |
| 5,512,882 A | 4/1996 | Stetter et al. |
| 5,580,794 A | 12/1996 | Allen |
| 5,708,247 A | 1/1998 | McAleer et al. |
| 5,820,551 A | 10/1998 | Hill et al. |

FOREIGN PATENT DOCUMENTS

| | | |
|---|---|---|
| EP | 0 351 891 B1 | 1/1990 |
| EP | 0 470 649 A2 | 2/1992 |
| EP | 0 213 825 A2 | 11/1992 |
| EP | 0 593 096 A2 | 4/1994 |

ELECTROCHEMICAL TEST DEVICE AND RELATED METHODS

REFERENCE TO RELATED APPLICATIONS

The present application is a divisional of U.S. patent application Ser. No. 10/224,875 filed Aug. 21, 2002 now U.S. Pat. No. 7,018,848, which is a continuation application of U.S. patent application Ser. No. 08/876,812 filed Jun. 17, 1997, now U.S. Pat. No. 6,638,772, which claims the benefit of U.S. Provisional Application 60/019,864 filed Jun. 17, 1996, all of which are hereby incorporated by reference in their entireties.

BACKGROUND OF THE INVENTION

1. Field of the Invention

The present invention relates to an electrochemical test device suitable for determining the presence or concentration of chemical and biochemical components (analytes) in aqueous fluid samples and body fluids such as whole blood. Additionally, this invention relates to a method of using such test devices for determining the presence or concentration of an analyte and to processes for preparing such a test devices.

2. State of the Art

Medical studies have demonstrated that the incidence of serious complications resulting from diabetes, such as vision loss and kidney malfunction, can be significantly reduced by careful control of blood glucose levels. As a result, millions of diabetics use glucose testing devices daily to monitor their blood glucose concentrations. Additionally, a wide variety of other blood testing devices are used to determine the presence or concentration of other analytes, such as alcohol or cholesterol, in aqueous samples, such as blood.

Such blood testing devices typically employ either a dry chemistry reagent system or an electrochemical method to test for the analyte in the fluid sample. In recent years, electrochemical testing systems have become increasingly popular due to their small size and ease of use. Such electrochemical testing systems typically use electrochemistry to create an electrical signal which correlates to the concentration of the analyte in the aqueous sample.

Numerous electrochemical testing systems and related methods are known in the art. For example, European Patent Publication No. 0 255 291 B1, to Birch et al., describes methods and an apparatus for making electrochemical measurements, in particular but not exclusively for the purpose of carrying out microchemical testing on small liquid samples of biological, e.g. of clinical, origin.

European Patent Publication No.0 351 891 B1, to Hill et al., teaches a method of making an electrochemical sensor by printing. The sensor is used to detect, measure or monitor a given dissolved substrate in a mixture of dissolved substrates, most specifically glucose in body fluid.

U.S. Pat. No. 5,391,250, to Cheney II et al., teaches a method of fabricating thin film electrochemical sensors for use in measuring subcutaneous or transdermal glucose. Fabrication of the sensors comprises placing a thin film base layer of insulating material onto a rigid substrate. Conductor elements for the sensors are formed on the base layer using contact mask photolithography and a thin film cover layer.

U.S. Pat. No. 5,437,999, to Diebold et al., teaches a method of fabricating thin film electrochemical devices which are suitable for biological applications using photolithography to define the electrode areas. The disclosures of each of the above patent specifications are incorporated herein by reference in their entirety.

An excellent reference on materials and process for fabricating electronic components is Charles A. Harper, Handbook of Materials and Processes for Electronics, 1984, Library of Congress card number 76-95803. It provides detail process information on thick film, thin film and photoresist processes.

Existing electrochemical testing systems, however, have certain limitations from the perspective of the end user or the manufacturer. For example, some electrochemical testing systems are difficult or costly to manufacture. As a result, such devices are too expensive to be used on a daily basis by, for example, diabetics. Other electrochemical testing systems are not sufficiently accurate to detect certain analytes at very low concentrations or to give reliable measurements of the analyte's concentration. Additionally, many electrochemical devices are too large to be easily carried by those needing to test their blood on a regular basis throughout the day. Thus, a need exists for improved electrochemical test devices.

SUMMARY OF THE INVENTION

The present invention utilizes amorphous semiconductor materials and semiconductor and printed circuit board (PCB) manufacturing techniques to provide an electrochemical test device suitable for determining the presence or concentration of analytes in aqueous fluid samples. By using amorphous semiconductor materials and PCB manufacturing techniques, uniform electrochemical test devices having well-defined reproducible electrode areas can be manufactured economically.

In particular, the test devices of this invention have very uniform surface areas which reduces the variability of the electrochemical test. In this regard, it has been found that the surface area of the electrodes and the accuracy of applying the reagent are critical to producing an accurate test. If the surface area is not consistent from test to test then each of the test devices must be individually calibrated to insure accurate readings. The test devices of the present invention permit highly accurate electrochemical analyte measurements to be performed on very small aqueous fluid samples without the need for individual calibration of each test device. The present inventions provide for the accurate reproduction of the test devices by using controlled deposition methods, such as sputtering, and chemical machining methods to accurately form the geometries of consistent size and shape from device to device in continuous production. These devices can also be readily manufactured due to the lower cost and the flexible nature of the amorphous semiconductor materials which facilitates production by continuous roll processing versus the step and repeat printing methods currently employed. The ability to use continuous processing to fabricate the device, such as continuous processes utilizing continuous roll coating, continuous roll sputtering, continuous photolithography systems utilizing contact masks and flow through baths, results in high volume manufacturing capability and substantial cost reductions over the step and repeat processes. Additionally, the amorphous nature of the conductors electrodes and constructed and used according to this invention eliminates problems found in prior test devices which utilize conventional conductor and semiconductor materials, which are crystalline in nature or are noble metals and, as a result, require flat and rigid substrates to prevent cracking during manufacture, distribution or use.

Dry electrochemical test devices fall into two primary configurations. The first configuration utilizes two electrodes, i.e., a working electrode and a counter electrode. The second configuration utilizes three electrodes, i.e., a working electrode, a counter electrode and a reference electrode. The use of the reference electrode and a reference material provides a fixed reference for the test. The test devices of the present invention can be of either configuration.

Accordingly, in one of its aspects, the present invention provides an electrochemical test device for determining the presence or concentration of an analyte in an aqueous fluid sample, said electrochemical test device comprising:

(a) a non-conductive surface;

(b) a working electrode comprising an amorphous semiconductor material affixed to the non-conductive surface, said working electrode having an first electrode area, a first lead and a first contact pad;

(c) a counter electrode comprising an amorphous semiconductor material affixed to the non-conductive surface, said counter electrode having an second electrode area, a second lead and a second contact pad; and (d) a reagent capable of reacting with the analyte to produce a measurable change in potential which can be correlated to the concentration of the analyte in the fluid sample, said reagent overlaying at least of portion of the first electrode area of the working electrode.

In another embodiment of this invention, the test device further comprises a reference electrode comprising an amorphous semiconductor material affixed to the non-conductive surface, said reference electrode having a third electrode area, a third lead, and a third contact pad, and wherein at least a portion of the third electrode area is overlaid with a reference material. Preferably, the reference material is a silver/silver chloride layer, a mercury/mercury chloride layer or a platinum/hydrogen material.

The non-conductive surface used in the test device of this invention can be any rigid or flexible material which has appropriate insulating and dielectric properties such as ceramics, polymeric board materials, flexible polymer sheets and the like.

Preferably, the non-conductive surface comprises a non-conductive coating affixed to one side of a flexible substrate comprising a metallic sheet material or a polymeric sheet material, such as polyester, polycarbonate and polyimide sheets or films. Preferred metallic sheets are metal foils which include aluminum, copper and stainless steel foil. Aluminum and stainless steel foil are particularly preferred.

The non-conductive coating used in the electrochemical test device is preferably an epoxy resin. The purpose of this coating is to provide a non-conductive barrier between the base material and the conductive layer and to improve the flatness of the surface morphology of the non-conductive surface on which the amorphous semiconductor electrodes are formed according to this invention. Better surface morphology of the non-conductive layer and the amorphous semiconductor electrodes provides improved accuracy of test results and consistency of performance.

Preferably, the amorphous semiconductor material used in this invention is amorphous silicon oxide. More preferably, the amorphous silicon oxide is doped with lithium, potassium, or a similar conducting ion to increased conductivity. Doping with lithium is particularly preferred. However, amorphous carbon, gold, silver or other conductor materials which do not interfere with the electrochemistry of the reagent system are also suitable. The amorphous semiconductor material can be applied by using various techniques including sputtering, evaporation, vapor phase deposition or other thin film deposition technique to form a conductive layer on the non-conductive surface, and technology can be used to form the electrodes. Thick film technologies can also be employed when using processes which control the application of the material and provide for uniform surface morphology. The surface texture of the amorphous semiconductor material is preferably less than 13 microinches or 0.33 microns. However, rougher textures can be used depending on the accuracy of the desired test device.

The reagent employed in the electrochemical test device is typically selected based on the analyte to be tested and the desired detection limits. The reagent preferably comprises an enzyme and a redox mediator. When the analyte to be detected or measured is glucose, the enzyme is preferably glucose oxidase and the redox mediator is potassium ferrocyanide.

In a preferred embodiment of this invention, the test device further comprises a blood separating membrane. The blood separating membrane separates whole blood samples into highly colored and relatively clear fluid portions before analysis. The blood separating membrane effectively blocks or filters red blood cells and allows essentially clear fluid to pass to the test electrodes. As a result, the analyte is measured in the clear fluid portion of the sample contacting the electrodes thereby substantially eliminating the red blood cells from the reaction and minimizing interference from the cells present in blood. This embodiment has the additional benefit of keeping the test site from drying out and thereby improves the performance of test devices designed for small sample sizes, such as in the 1 to 5 microliter range.

The electrochemical test device of the present invention is used to determine the presence or concentration of an analyte in an aqueous fluid sample. Accordingly, in one of its method aspects, the present invention provides a method for determining the presence or concentration of an analyte in an aqueous fluid sample, said method comprising:

(a) providing an electrochemical test device comprising: (i) a non-conductive surface; (ii) a working electrode comprising an amorphous semiconductor material affixed to the non-conductive surface, said working electrode having an first electrode area, a first lead and a first contact pad; (iii) a counter electrode comprising an amorphous semiconductor material affixed to the non-conductive surface, said counter electrode having a second electrode area, a second lead, and a second contact pad; and (iv) a reagent capable of reacting with the analyte to produce a measurable change in potential which can be correlated to the concentration of the analyte in the fluid sample, said reagent overlaying at least of portion of the first electrode area of the working electrode;

(b) inserting the electrochemical test device into a meter device;

(c) applying a sample of an aqueous fluid to the first electrode area of the working electrode;

(d) reading the meter device to determine the presence or concentration of the analyte in the fluid sample.

In another embodiment, the test device employed in this method further comprises a reference electrode comprising an amorphous semiconductor material affixed to the non-conductive surface, said reference electrode having a third electrode area, a third lead, and a third contact pad, and wherein at least a portion of the third electrode area is overlaid with a reference material. Preferably, the reference material is a silver/silver chloride layer, a mercury/mercury chloride layer or a platinum/hydrogen material. Silver/silver chloride is a particularly preferred reference material.

The non-conductive surface may be any rigid or flexible material having appropriate insulating and dielectric properties, as mentioned above. Preferably, the non-conductive surface is provided by affixing a non-conductive coating to one side of a substrate, which substrate is preferably a flexible metallic sheet material or a polymeric sheet material.

As discussed above, the present invention utilizes amorphous semiconductor materials and PCB manufacturing techniques to provide electrochemical test devices. This film or thick film methods and technologies can be used to create the amorphous semiconductor material conductive layers and electrodes according to this invention. Accordingly, in one of its process aspects, the present invention provides a process for preparing an electrochemical test device suitable for determining the presence or concentration of an analyte in an aqueous fluid sample, said process comprising the steps of:

(a) providing a non-conductive surface;

(b) depositing an amorphous semiconductor material on said surface to form a conductive layer;

(c) chemically machining the conductive layer to form a working electrode comprising a first electrode having a first electrode area, a first lead and a first contact pad, and to form a counter electrode comprising a second electrode having a second electrode area, a second lead and a second contact pad;

(d) applying a reagent to at least a portion of the first electrode area of the working electrode, said reagent being capable of reacting with an analyte in an aqueous fluid sample to produce a measurable change in potential which can be correlated to the concentration of the analyte in the fluid sample.

In another embodiment, step (c) of this process further comprises forming a reference electrode comprising a third electrode having a third electrode area, a third lead and a third contact pad.

Preferably, the non-conductive surface is provided by affixing a non-conductive coating to one side of a substrate, which substrate is preferably a flexible metallic sheet material or a polymeric sheet material. Accordingly, in a preferred embodiment, step (a) above comprises the steps of:

(f) providing a flexible substrate; and (g) applying a non-conductive coating to the substrate to form a non-conductive surface.

In another preferred embodiment, step (c) above comprises the steps of:

(h) applying a photoresist to the conductive layer to form a first photoresist layer;

(i) positioning a first developer mask on the first photoresist layer;

(j) exposing the unmasked first photoresist layer to ultraviolet light to form a first patterned photoresist area;

(k) removing the first developer mask;

(l) removing the first photoresist layer not exposed to ultraviolet light with a developer to form a first exposed conductive layer;

(m) contacting the first exposed conductive layer with a chemical etchant to remove the first exposed conductive layer; and (n) removing the first patterned photoresist area with a solvent to form a second exposed conductive layer, said second exposed conductive area comprising (i) a working electrode comprising a first electrode having a first electrode area, a first lead and a first contact pad, (ii) a counter electrode comprising a second electrode having a second electrode area, a second lead and a second contact pad, and optionally (iii) a reference electrode comprising a third electrode having a third electrode area, a third lead and a third contact pad.

In further preferred embodiment, step (c) above further comprises the steps of:

(o) applying a photoresist to the second exposed conductive layer to form a second photoresist layer;

(p) positioning a second developer mask on the second photoresist so that the second photoresist layer covering the third electrode area is masked;

(q) exposing the unmasked second photoresist layer to ultraviolet light to form a second patterned photoresist layer;

(r) removing the second developer mask;

(s) removing the second photoresist layer not exposed to ultraviolet light with a developer to expose the third electrode area;

(t) applying a reference material the third electrode area;

(u) removing the second patterned photoresist layer with a solvent.

Preferably, the process employed to prepare the test devices of this invention is a continuous process. The ability to use continuous processing to fabricate the test devices, such as a continuous process utilizing continuous roll coating, continuous roll sputtering, continuous photolithography systems utilizing contact masks and flow through baths, results in high volume manufacturing capability and substantial cost reductions over the step and repeat processes.

DETAILED DESCRIPTION OF THE INVENTION

Figure 1A:
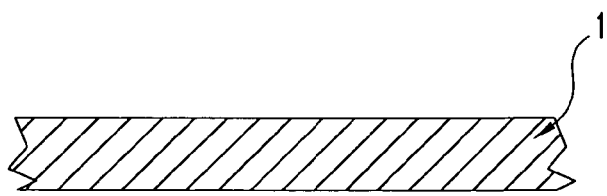
FIGS. 1A, 1B, 1C and 1D illustrate the manufacturing process from substrate or non-conductive surface to photoresist.

The present invention utilizes amorphous semiconductor materials and semiconductor and printed circuit board (PCB) manufacturing techniques to provide an electrochemical test device suitable for determining the presence or concentration of analytes in aqueous fluid samples. By using amorphous semiconductors and PCB manufacturing techniques, uniform electrochemical test devices having well-defined reproducible electrode areas can be manufactured economically. These areas have very uniform surface morphology which reduces the variability of the electrochemical test. The surface morphology is directly related to the surface area of the electrodes. The amount and concentration of applied reagents are also critical to producing an accurate test. If the surface area is not consistent from device to device then the individual devices manufactured have to be individually calibrated to insure accurate readings in a meter. The test devices of the present invention permit highly accurate electrochemical analyte measurements to be performed on very small aqueous fluid samples due to the accurate reproduction of the test devices using controlled deposition methods such as sputtering, vapor phase deposition, glow discharge methods or evaporation and PCB chemical machining methods to form the geometries. These devices can also be readily manufactured due to the lower cost and flexible nature of the amorphous semiconductor materials which allow the use of volume production in continuous processing manufacturing methods.

Thin film technologies are preferred for forming the amorphous semiconductor material layer or coating, such as sputtering, vapor phase deposition, glow discharge methods or evaporation. Such processes are capable of producing coatings up to a thickness of a few microns and of applying the coatings uniformly over the entire surface. If desired, thick film technologies are capable of producing much thicker layers in the range of less than 0.005 inches. While both methods can produce uniform surfaces, thin film surface morphology is dependent on the surface roughness of the underlying substrate, whereas the thick film technologies are capable of changing the final surface morphology of the device due to their thicker structure.

The electrochemical test device of this invention employs at least two types of electrodes. The first type of electrode is referred to as the "working or indicating electrode" and the second type is referred to as the "counter or opposing electrode". These electrodes permit changes in potential between the electrodes to be accurately measured when the analyte is applied across the electrodes, where one of the electrodes has on its surface a reagent reactive with the analyte. Optionally, the test device may also contain a reference electrode. The reference electrode allows accurate measurements of potential to be made with respect to a fixed reference point. Any suitable reference electrode may be used, include silver/silver chloride, mercury/mercury chloride and platinum/hydrogen reference electrodes. Preferably, the reference electrode is a silver/silver chloride reference electrode and the working electrode has a potential ranging from about +1 to −1 volts versus the reference electrode. Reference electrodes suitable for use in this invention are further described in R. S. C. Cobbold, *Transducers for Biomedical Measurements: Principles and Applications*, pp. 343–349, John Wiley & Sons (New York).

The electrodes in the test device of this invention are preferably supported on a flexible support material or substrate. Any suitable dielectric material may be used as the substrate. For example, the substrate may be selected from a polymeric sheet, film or foil material, such as a polyester, a polycarbonate, or a polyimide support material. Such polymeric materials are well known in the art and are commercially available. Typically, such polymeric support materials are annealed at a temperature ranging from about 200 to about 220° F. (about 90 to 105° C.) prior to use. Such an annealing process preshrinks the substrate thereby reducing the effects of shrinkage during subsequent processing. Alternatively, the substrate may be a metal foil having a thickness ranging from about 0.0005 to about 0.005 inches. Flexible metal sheet materials can be used, but must be coated with a dielectric coating. Preferred metal sheets include, foils such as aluminum, copper and stainless steel foils. Aluminum and stainless steel foils are particularly preferred.

The substrate employed in this invention, whether ceramic, polymeric or metallic, is preferably coated with a surface coating material prior to further use to improve the surface morphology of the substrate. Suitable surface coating materials include, by way of example, ink, paint, clay base coating materials and epoxy resins. When metal foil is used as the substrate, the surface coating is preferably an epoxy coating. Preferred epoxy resins have a high temperature resistance and include, by way of example, epoxy anhydrides (Dicy), phenolic epoxy resins, and polyamide epoxy resins (such as VERSAMIDES), available from Conat, Inc.

The surface coating material may be applied to the substrate by any conventional method, such as roll coating, knife over roll, slot coating, reverse roll, lip coating, spin coating or any another coating method or technique which applies a thin layer of surface coating material sufficient to fill the surface valleys of the substrate. Preferably, the surface coating material is applied to the substrate such that the surface coating is less than about 0.005 inches in thickness. In addition to providing an improved surface flatness by reducing the variation on surface morphology, the surface coating increases the bonding of the conductive layer to the substrate and provides a non-conductive barrier between the substrate and the electrodes formed on the surface coating material.

The electrodes are then prepared on the coated substrate using semiconductor and printed circuit board manufacturing techniques. Typically, a conductive layer is first deposited on or applied to the coated substrate. The conductive layer comprises an amorphous semiconductor material, such as amorphous silicon oxide, amorphous carbon, gold or silver and the like. Amorphous metals can be formed by permitting a small amount of helium gas to escape in the sputtering chamber during sputtering. Such materials are well known in the art. For example, formation of suitable amorphous semiconductor films are described in U.S. Pat. No. 4,226,898, to Ovshinsky, the disclosure of which is incorporated herein by reference in its entirety.

Preferably, the amorphous semiconductor material employed in this invention is doped with lithium, potassium, or a similar conducting ion to increased conductivity. U.S. Pat. Nos. 3,983,076, and 4,178,415, to Ovshinsky, describe suitable methods for adding various compounds to amorphous semiconductor material to increase its conductivity. The disclosures of these patents are incorporated herein by reference in their entirety.

The amorphous semiconductor material is preferably deposited on the non-conducting coating or substrate to form a conductive layer having a thickness of less than about 0.005 inches, more preferably a thickness ranging from about 1 to about 5 microns. The amorphous semiconductor material may be applied to the non-conducting coating or substrate using any art recognized procedure to form a conductive layer, such as sputtering, vapor phase deposition, glow discharge deposition, evaporation and the like. Alternatively, other deposition techniques such as electroplating, thick film laminating, roll transfer and the like may be employed. Thinner films are best achieved by sputtering, evaporation, vapor phase deposition, glow discharge methods or other thin film deposition method whereas thicker films are best formed using thick film deposition techniques such as electroplating, thick film laminating, roll transfer and the like. Charles A. Harper, *Handbook of Materials and Processes for Electronics*, 1984, (Library of Congress card number 76-95803) discusses various methods of forming thin films in Chapter 11, describes various thick film process in Chapter 12 and is devoted to photoresist processing in Chapter 14.

Preferably, the amorphous semiconductor material is deposited using vapor phase deposition or sputtering techniques. In a particularly preferred embodiment, the amorphous semiconductor material is formed by codeposition of the amorphous semiconductor material and the doping material such as by co-vacuum deposition or cosputtering. Cosputtering can be accomplished in a conventional r.f. sputtering system, such as available from ULVAX Vacuum Systems. In this process, a cathode or target is bonded to a standard aluminum backing plate and is made of the semiconductor material to be deposited. Also, pieces of the doping material are secured to the cathode or target. Substrates upon which the amorphous semiconductor material and the doping material are to be deposited are carried by a holder located from the target by a distance of about 3.5 cm for a 3 ⅓" diameter cathode or passed continuously by the target.

The sputtering machine is first evacuated to a vacuum pressure somewhat less than about $6 \times 10^{-6}$ torr to provide a background vacuum pressure. Argon is bled into the machine to provide an operating pressure of about $5 \times 10^{-3}$ torr as determined by a reading on a Pirani vacuum gauge, giving an actual vacuum pressure of about $7 \times 10^{-3}$ torr in the machine. The surface of the cathode or target and pieces of doping material are first cleaned by sputtering against the shutter of the machine adjacent to substrates for about 30 minutes. Thereafter, the shutter is opened and the semiconductor material of the target and the pieces of doping material on the target are cosputtered onto the non-conductive coating or substrate. The cathode or target and the holder for the substrates are both water cooled so that their temperature is low during the sputtering operation, as for example, approximately 50° C. The r.f. power of the machine may have a frequency of about 13.56 MegaHertz, and about 1000 Volts of forward power, about 50–70 Watts being utilized for 3.5" diameter cathode or target.

The deposition rates depend upon the materials being sputtered, and the time of deposition is varied to obtain desired thicknesses of the deposit. The thicknesses of the simultaneously deposited amorphous semiconductor film having the doping material therein may vary from a few 100 Å to about 5μ, depending upon the uses to which the amorphous semiconductor film is to be put. The amorphous semiconductor material is deposited on the non-conductive coatings or substrates in amorphous form.

The amount of doping material homogeneously incorporated in the amorphous semiconductor material is generally determined by the area of the pieces of the doping material applied to the semiconductor material of the cathode or target. Desired percentage of modifier material added to the amorphous semiconductor material may accordingly be conveniently controlled. By utilizing cosputtering as generally here described, the doping material is substantially homogeneously incorporated in the semiconductor material to provide the beneficial features of this invention.

Preferably, the amorphous semiconductor material is applied continuously to the non-conductive coating or substrate using art recognized continuous processes. Such continuous processes are described, for example, in U.S. Pat. No. 3,983,076, to Rockstad, and in U.S. Pat. Nos. 3,271,591 and 4,178,415, to Ovshinsky, the disclosures of which are incorporated herein by reference in their entirety. The ability to use continuous processing to fabricate the test devices of this invention, such as a continuous process utilizing continuous roll coating, continuous roll sputtering, continuous photolithography systems utilizing contact masks and flow through baths, results in high volume manufacturing capability an substantial cost reductions over the step and repeat processes currently used. Suitable machines for such continuous processes are made by Ulvac Vacuum Systems of Japan.

After the amorphous semiconductor material has been deposited on the non-conductive coating or substrate, conventional photolithography techniques or other electronic circuit fabrication technologies are used to form the electrodes. In the first step of a typical process, a photoresist material is applied to the conductive layer and dried. Any suitable photoresist material may be employed, including both negative and positive photoresist materials. A preferred material is the negative semi-aqueous resist available from Dupont under the tradename "Resiston".

A developer mask is then positioned over the photoresist layer. The mask can be either a contact or non-contact type. The patterning and masking methods that can be employed to form the electrode shapes, conductive lines, contact pads, etc., according to this invention can include mechanical masks, contact masks and the like, as well as other methods useful herein. For example, Chapter 14 of the above mentioned Harper, *Handbook of Materials and Processes for Electronics*, can be referred to for such methods. The developer mask, which has cutout portions in the shape of the electrodes, only covers a portion of the photoresist layer leaving a portion of photoresist layer exposed. The uncovered or exposed photoresist layer is then irradiated with ultraviolet (UV) light. Upon exposure to ultraviolet light, the photoresist material becomes insoluble in the developer solvent. The UV-exposed, insoluble photoresist material is termed "patterned photoresist". The developer mask is then removed and the photoresist layer is contacted with developer to remove the photoresist material previously covered by the developer mask. The developer used in this step will vary depending on the particular photoresist material employed. Typically, the proper developer for use with a particular photoresist will be specified by the manufacturer of the resist material. When "Resiston" is used as the photoresist, the developer/solvent recommended by Dupont should be employed and careful attention paid to recommended procedures. If an alternate photoresist is selected, such as Shipley "AZ-11", then an alternate developer would be used to remove the unexposed photoresist.

A chemical etchant is then used to remove the conductive layer no longer protected by the photoresist material. The chemical etchant does not remove the conductive material still protected by the remaining exposed, insoluble photoresist layer. Suitable chemical etchants include hydrofluoric acid (HF) or ammonium fluoride/hydrofluoric acid ($NH_4F$—HF) mixtures. A solvent is then applied to the patterned photoresist areas defining the electrodes to remove the patterned photoresist layer. Suitable solvents for removing the photoresist layer include, by way of example, sulfuric acid/dichromate or ammonia/hydrogen peroxide. Treatment with the solvent exposes the surface of the amorphous semiconductor electrodes. Each electrode comprises three areas: a contact pad, a lead and an electrode area. Preferably, after exposure of the electrodes, the leads of each electrode are insulated by applying an epoxy resin material to the leads.

Optionally, the third electrode, if present, is then converted into a reference electrode by applying a suitable reference material. Suitable reference materials include silver/silver chloride, a mercury/mercury chloride and platinum/hydrogen materials. Such materials can be applied to the third electrode area of the reference electrode by any thin film deposition method described above.

A particularly preferred reference material is silver/silver chloride. In order to obtain consistent results from device to device, the silver/silver chloride layer must be applied such that the silver/silver chloride layer covers essentially the same surface area in each device manufactured. Preferably, this is accomplished using photolithography techniques as described above to expose a precise area of the electrode after developing. A thin layer of silver is then deposited on the exposed area, preferably by sputtering or other consistent film application method. The silver layer is preferably less than about 0.001 inches in thickness, more preferably about 1 micron to about 5 microns in thickness. Alternatively, a silver layer can be applied to the electrode area of the reference electrode using pad printing, inkjet methods, transfer roll printing or similar techniques. The silver layer is then contacted with $FeCl_3$ solution to convert the silver surface to silver chloride thereby forming a silver/silver chloride layer. Subsequent removal of the photoresist using a solvent completes the formation of the reference electrode.

The electrochemical test device is then completed by applying an appropriate reagent to the working electrode. Suitable reagents for determining the presence or concentration of various analytes are well known in the art and are described in further detail herein below.

Preferred Process for Preparing the Electrodes

As described above, the electrodes for the electrochemical test device of this invention are prepared using amorphous semiconductor materials and semiconductor and printed circuit board manufacturing techniques. Preferably, such electrodes are formed in a continuous manner. A preferred process for the preparation of electrodes suitable for use in this invention is illustrated in FIGS. 1–5.

As illustrated in cross section FIG. 1A, a thin support material 1 of aluminum foil 0.005 inches thick is employed.

Figure 1B:
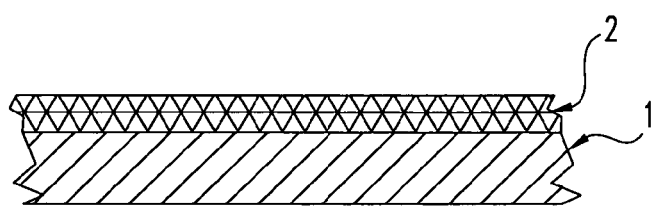

Cross section FIG. 1B shows the substrate after being coated with epoxy 2 using a lip coater available from Hirano. The thickness of the epoxy 2 is 0.001 to 0.005 inches. The epoxy is thoroughly dried prior to the next step of the process.

Figure 1C:
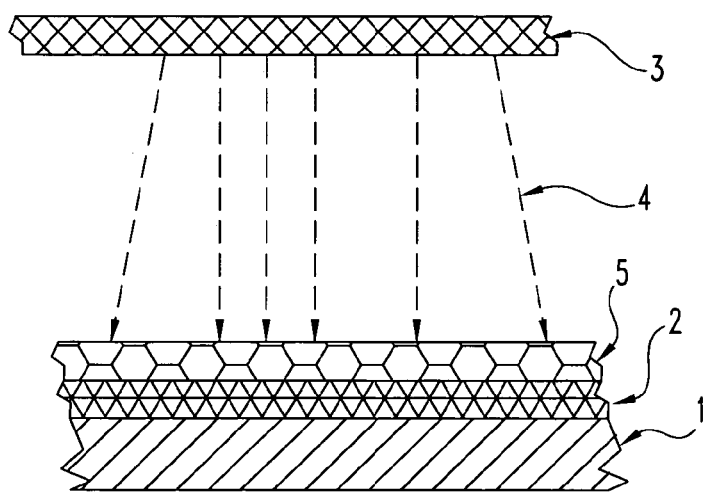

Cross section FIG. 1C shows the substrate formed from support material 1 and epoxy 2 in a sputtering apparatus where an amorphous silicon oxide layer 5 is applied to the epoxy 2. The target 3 and plasma 4 create an amorphous silicon layer 5 with a thickness of less than about 0.005 inches and preferable in the range of 1 to 5 microns.

Figure 1D:
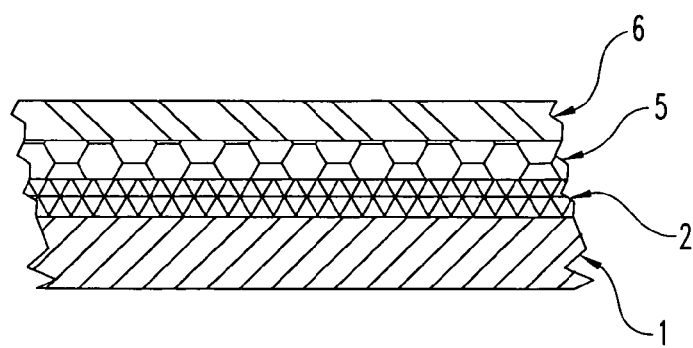

As shown in cross section FIG. 1D after applying the amorphous silicon layer 5, a photoresist layer 6 is applied to the composite. A suitable negative semi-aqueous resist from Dupont, "Resiston" is appropriate for use in this invention. The resist is applied by a hot roll lamination process.

Figure 2A:
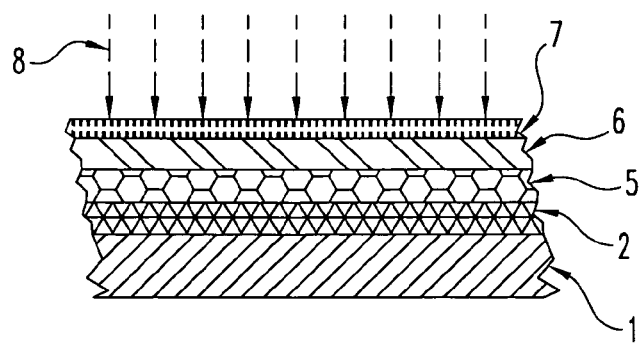
FIGS. 2A, 2B, 2C and 2D illustrate the manufacturing process from photoresist to solvent application resulting in a finished working or counter electrode.

As illustrated in cross section FIG. 2A, a photomask 7 having a selected cutout pattern for the desired electrode and circuit lines and ultraviolet light 8 are then applied to the composite which is baked as specified by the Dupont product directions. The photoresist that was exposed to the ultra violet light is now insoluble to the developer.

Figure 2B:
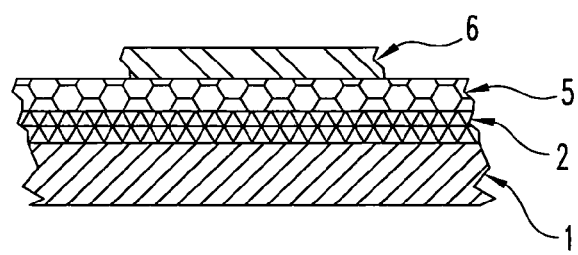

The composite shown in cross section FIG. 2B is after processing in the developer to expose portions of the amorphous silicon oxide layer 5. The entire composite is then placed in a chemical etchant bath and the exposed areas of the amorphous silicon layer 5 shown in FIG. 2B are removed.

Figure 2C:
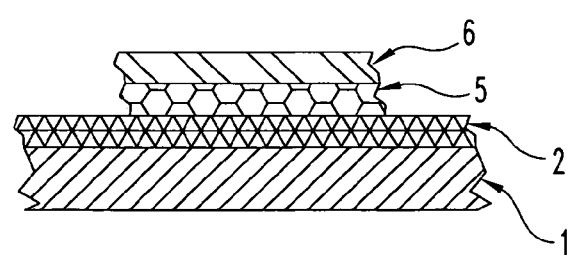

As shown in cross section FIG. 2C, the chemical etchant bath removes unwanted amorphous silicon oxide layer 5 leaving a composite of support material 1, epoxy 2, selective areas of amorphous silicon oxide 5 and photoresist 6. The etchant is unable to dissolve the area of amorphous silicon layer 5 covered by the photoresist layer 6.

Figure 2D:
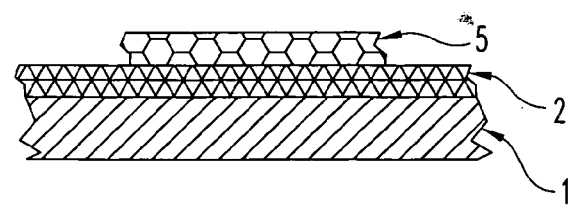

As shown in cross section FIG. 2D, the activated or patterned photoresist layer 6 is then removed by applying a solvent which exposes the amorphous silicon layer 5, leaving the desired electrode and conductive lines on epoxy 2.

Figure 3:
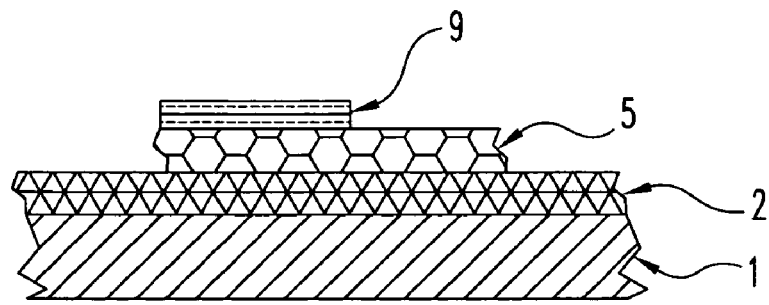
FIG. 3 illustrates finished reference electrode.
Figure 4:
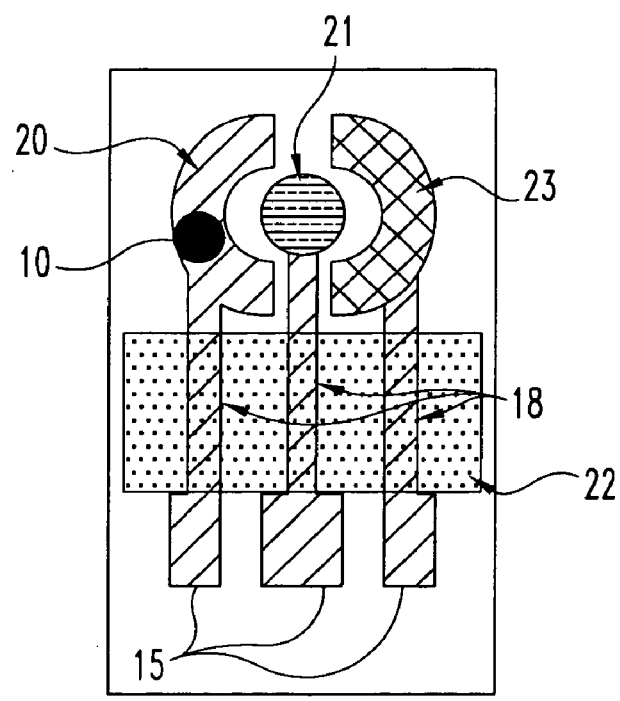
FIG. 4 illustrates a plan view of a test device having working, counter and reference electrode.

Cross section FIG. 3 shows the reference electrode 21 after a silver/silver chloride material layer 9 has been applied. Precise application of the silver/silver chloride layer is extremely important and needs to be controlled so that the surface area is constant and consistent from device to device. This is accomplished by applying a photoresist similarly to previous steps and processing the electrodes so that only the reference electrode 21 as shown in FIG. 4 is exposed after developing. The part is then sputtered with a thin layer of silver less than 0.001 inches in thickness over the reference electrode 21 formed from amorphous silicon oxide 5. The preferred thickness of the silver is between 1 and 5 microns of silver. Thinner conductors can be used as long as the system is controlled and surface morphology is consistent. The part is then treated with $FeCl_3$ to convert the silver surface to silver chloride 9.

Plan view of FIG. 4 shows the exposed amorphous silicon layer 5 which defines the electrodes, including the contact pads 15, leads 18 and working electrode 20, reference electrode 21 and counter electrode 23. The lead lines 18 are then insulated by applying an epoxy 22. Reagent 10 is applied to working electrode 20 after the silver/silver chloride layer is applied to reference electrode 21.

Figure 5C:
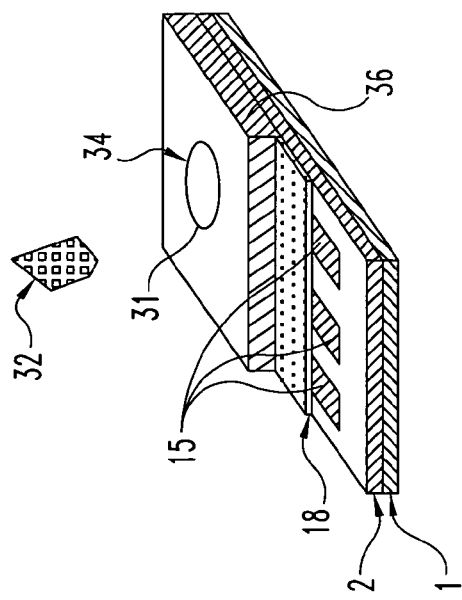
FIGS. 5A, 5B and 5C illustrate the device of FIG. 4 with a blood separating membrane.
Figure 5B:
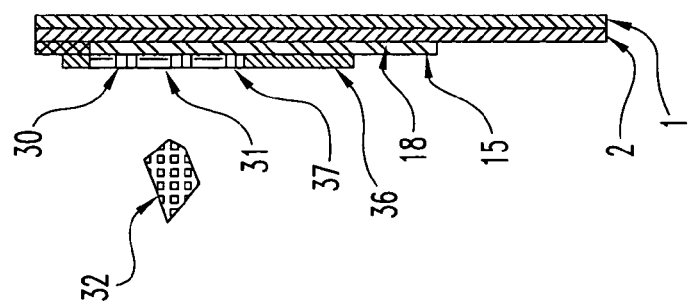
Figure 5A:
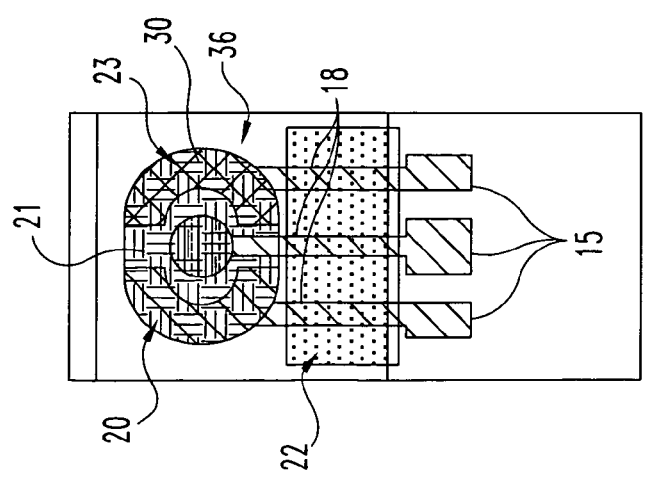

Plan view FIG. 5A shows the preferred embodiment using a blood separation membrane 30 of this invention. Membrane 30 preferably has a skin side 31 adapted to block or filter red blood cells and a non-skin or opposite side 37. Cross section view FIG. 5B shows that the skin side 31 of the membrane 30 is applied so that the skin side can receive the blood sample 32. Perspective view FIG. 5C shows the membrane 30 has been embossed so it is forced into hole 34 in handle or cover 36. Handle 36 is made of any suitable dielectric material such as PET, polystyrene, or acrylic and must be as thick as the membrane. The membrane is glued to the handle 36 from the underside of handle 36 and to epoxy layer 22 which insulates the leads 18 using adhesive 38 as shown in FIG. 5B. A separating agent is imbibed and dried to the membrane 30 prior to applying the membrane as shown in FIG. 5C. In this embodiment the side 37 opposite the skin side 31 of the membrane 30 is in communication with electrodes 20, 21 and 23 as shown in FIG. 5A. To insure communication between the two layers, the assembly process during manufacture includes applying mechanical pressure to the skin side 31 of the membrane 30 to force the two layers together so that they contact each other as shown in FIG. 5B.

Reagents

Various types of analytical or electrochemical sensor reagents may be applied to the electrodes. To create a functional electrochemical test device, a reagent chemistry must be selected based on the analyte to be tested and the desired detection limits. Preferably, the reagent is deposited on the specific electrodes such that a uniform amount is applied from sensor to sensor and the reagent is applied uniformly over the appropriate electrodes. The reagent may be applied using any conventional procedure, such as screen printing, inkjet printing, or discrete application using IVEK pumps or any other drop on demand system capable of delivering consistent and uniform volume of reagent.

The specific electrodes coated will depend on the specific reagent(s) employed. Typically, the reagent is applied to the working electrode, but may in some cases also be applied to the other electrodes. After the reagent has been placed on the appropriate electrodes, it is typically dried. Subsequently, when the test device is used, the test sample of aqueous fluid, such as blood, rehydrates the reagent and a potential is applied to the electrodes from which a current measurement may be taken by a meter.

An example reagent formulation suitable for use in the present invention is described below. This reagent may be used to determine the presence or concentration of glucose in an aqueous fluid sample. Preferably, this reagent formulation is used with an electrochemical sensor having an counter electrode 20, working electrode 23 and reference electrode 21.

Reagent Formulation

| Material | Amount/Concentration |
|---|---|
| 2-(N-morpholino)ethanesulfonic acid (MES buffer) | 100 millimolar (mM) |
| Triton X-100 | 0.08% wt/wt |
| Polyvinyl alcohol (PVA) mol. wt. 10K 88% hydrolized | 1.00% wt/wt |
| Imidazole osmium mediator, reduced, as defined in U.S. Pat. No. 5,437,999 | 6.2 mM |
| Glucose Oxidase | 6000 units/mL |

The above reagent formulation may be prepared using the following procedures:

(a) 1.952 grams of MES buffer is added to 85 mL of nanograde water. The mixture is stirred until the components dissolve. The pH of the solution is adjusted to 5.5 with NaOH. The volume of the solution is then brought to 100 mL of final buffer solution.

(b) 0.08 grams of Triton X-100 and 1 gram of PVA is added to a beaker capable of holding all the components (e.g., a 200 mL beaker). The buffer solution is added to bring the total solution weight to 100 grams. The mixture is heated to boiling and stirred to dissolve the PVA.

(c) 4.0 mg of the reduced osmium mediator is added to 1 mL of the solution from step (b) above. The mixture is stirred to dissolve the mediator.

(d) The mixture is left to cool to room temperature.

(e) 6000 units of glucose oxidase are added and the mixture is mixed until the enzyme is dissolved.

The above reagent formulation may be used to determine the presence or concentration of glucose in an aqueous fluid sample. As will be apparent to those skilled in the art, other reagent formulations may be employed to assay different analytes. Such reagent formulations are well known in the art. Typically, such reagent formulations are designed to react specifically with the desired analyte to form a measurable electrochemical signal.

Without being limited to theory, it is believed that in the example reagent formulation described above, glucose is anaerobically oxidized or reduced with the involvement of the enzyme and the redox mediator. Such a system is sometimes referred to as an amperometric biosensor. Amperometry refers to a current measurement at constant applied voltage on the working electrode. In such a system, the current flowing is limited by mass transport. Therefore, the current is proportional to the bulk glucose concentration. The analyte, enzyme and mediator participate in a reaction where the mediator is either reduced (receives at least one electron) or oxidized (donates at least one electron). The glucose reaction ends when glucose oxidase is oxidized and the mediator is reduced. The mediator is then oxidized at the surface of the working electrode by the applied potential difference. Changes in the system amperage result from changes in the ratio of oxidized/reduced form of the redox mediator. The amperage change directly correlate to the detection or measurement of glucose in the test sample.

Various enzymes may be used in the reagent formulations employed in this invention. The particular enzyme employed will vary depending on the analyte to be detected or measured. Preferred enzymes include glucose oxidase, glucose dehydrogenase, cholesterol esterase and alcohol oxidase. The amount of enzyme employed will generally range from about 0.5 to about 3.0 million units of enzyme per liter of reagent formulation.

The reagent formulation will also typically contain a redox mediator. The redox mediator will generally be chosen to be compatible with the enzyme employed and combinations of redox mediators and enzymes are well known in the art. Suitable redox mediators include, by way of example, potassium ferricyanide and ferrocene derivatives, such as 1,1'-dimethyl ferrocene. The amount of redox mediator employed in the reagent formulation will typically range from about 0.15 M to about 0.7 M. Additional mediators suitable for use in this invention include methylene blue, p-benzoquinone, thionine, 2,6-dichloroindophenol, gallocyanine, indophenol, polyviologen, osmium bis(2,2'-bipyridine)dihydrochloride, and riboflavin-5'-phosphate ester. Optionally, these mediators can be chemically bound or entrapped in a matrix, such as a polymer, using procedures well known in the art.

Examples of enzyme/mediator combinations suitable for use in this invention include, but are not limited to, the following:

| Analyte | Enzyme | Mediator |
|---|---|---|
| glucose | glucose dehydrogenase | ferricyanide |
| glucose | glucose oxidase | tetracyanoquinodimethane |
| cholesterol | cholesterol esterase | ferricyanide |
| alcohol | alcohol oxidase | phenylenediamine |

A preferred reagent chemistry uses potassium ferricyanide as a mediator.

In addition to an enzyme and a redox mediator, the reagent layer on the electrode preferably further comprises a buffer, a stabilizer, a dispersant, a thickener or a surfactant. These materials are typically employed in amounts which optimize the reaction of the reagents with the analyte. The concentration ranges for these components referred to below are for the reagent formulation before it has dried on the electrode surface.

A buffer is preferably employed in the reagent formulation to provide a satisfactory pH for enzyme function. The buffer used must have a higher oxidation potential than the reduced form of the redox mediator. A preferred buffer for use in this invention is a phosphate buffer having a concentration ranging from about 0.1 M to about 0.5 M. Other suitable buffers include BES, BICINE, CAPS, EPPS, HEPES, MES, MOPS, PIPES, TAPS, TES and TRICINE buffers (collectively known as 'GOOD' buffers), citrate, TRIS buffer, and the like. The 'GOOD' and TRIS buffers are commercially available from Sigma-Aldrich, Inc. (St. Louis, Mo., USA).

A stabilizer may also be employed in the reagent formulation to stabilize the enzyme. When the enzyme used is glucose oxidase, a preferred stabilizer is potassium glutamate at a concentration ranging from about 0.01 to 4.0% weight. Other suitable stabilizers include succinate, aspartate, blue dextran and the like.

Additionally, dispersants may be used in the reagent formulation to enhance the dispersion of the redox mediator and to inhibit its recrystallisation. Suitable dispersants include microcrystalline cellulose, dextran, chitin and the like. Typically, the dispersant is used in the reagent formulation in an amount ranging from about 1.0 to about 4.5% weight. Preferred dispersants include, but are not limited to, AVICEL RC-591 (a microcrystalline cellulose available from FMC Corp.) and NATROSOL-250 M (a microcrystalline hydroxyethylcellulose available from Aqualon).

A thickener may also be employed in the reagent formulation to hold the reagent to the electrode surface. Suitable thickeners include water soluble polymers, such as polyvinylpyrrolidone.

Additionally, a surfactant may be added to the reagent formulation to facilitate rapid and total wetting of the electrode surface. Preferably, the reagent formulation contains a nonionic surfactant in an amount ranging from about 0.01 to 0.3% by weight. A preferred surfactant is TRITON X-100, available from Sigma-Aldrich, Inc.

Use of a Blood Separating Membrane

The electrochemical test device of this invention may be used to determine the presence or measure the concentration of an analyte in a blood sample. In a preferred embodiment, the electrochemical test device of this invention further comprises a separating membrane which separates whole blood samples into highly colored and relatively clear fluid portions before analysis. As a result, the analyte is measured in the clear fluid portion of the sample contacting the electrodes thereby substantially eliminating the red blood cells from the reaction.

Whole blood may be separated using a small piece of polyethersulfone membrane, such as Gelman P/N 200 D and the like, which has been treated with separating agents and dried. Such membranes are described in copending U.S. patent application entitled "Methods and Devices for Determination of an Analyte in a Body Fluid," Ser. No. 08/628,489 filed Apr. 5, 1996, the disclosure of which is incorporated herein by reference in its entirety. Suitable separating agents for use with the membrane include, but are not limited to, polyvinyl sulfonic acid (PVSA), polyethylene glycol (PEG), polystyrene sulfonic acid (PSSA), hydroxypropyl cellulose (commercially available as Klucel™-EF), polyvinyl alcohol (PVA), polyvinylpyrrolidone (PVP), polyacrylic acid (PAA), water soluble salts, citrates, formates, sulfates, amino acids, chitosan (amino sugar), citric acid, phytic acid, malic acid and the like. Such materials are described in further detail in U.S. Pat. No. 5,306,623, to Kiser et al, the disclosure of which is incorporated herein by reference in its entirety.

Use of the Electrochemical Test Device

To illustrate the use of an electrochemical test device of this invention, the following glucose assay is described. It will be understood, however, that by selecting the proper reagent, other analytes may be determined using these procedures.

The electrodes of the electrochemical test device are prepared as described above and the working electrode is coated with 1.0 μL of the above-described reagent formulation and dried.

The electrochemical test device is then inserted in a meter before the test sequence is initiated. Any suitable meter device which has contacts that interface with the test device contacts 15 (as shown in FIG. 5A) may be employed. Such metering devices are well known in the art. The meter will generally contain a measuring circuit and be adapted to apply an algorithm to the current measurement whereby the analyte level is provided and visually displayed. Examples of suitable power sources and meters may be found, for example, in U.S. Pat. Nos. 4,963,814, 4,999,632, and 4,999,582 to Parks et al., U.S. Pat. No. 5,243,516 to White et al., and European Patent Publication No. 89116797.5, to Hill et al. The disclosures of these patents are incorporated by reference herein in their entireties.

A small sample of blood or other aqueous fluid is then applied to the test device. The current is measured about 10 to about 30 seconds after applying the sample. The current is read by the meter between the working and counter electrode and, optionally, is compared to the reference electrode, if it is present. The meter then applies the algorithm to the current measurement and converts the measurement to an analyte concentration. This analyte level is visually displayed on the meter.

From the foregoing description, various modifications and changes in the electrochemical test devices, processes and methods of this invention will occur to those skilled in the art. All such modifications coming within the scope of the appended claims are intended to be included therein.

What is claimed is:

1. A process for preparing an electrochemical test device suitable for determining the presence or concentration of an analyte in an aqueous fluid sample, said process comprising the steps of:
   (a) providing a single substrate, the single substrate comprising a non-conductive coating affixed to one side of a flexible material;
   (b) depositing an amorphous semiconductor material on said non-conductive coating to form a conductive layer;
   (c) chemically machining the conductive layer to form a working electrode comprising a first electrode having a first electrode area, a first lead and a first contact pad, and to form a counter electrode comprising a second electrode having a second electrode area, a second lead and a second contact pad; and
   (d) applying a reagent to at least a portion of the first electrode area of the working electrode, said reagent being capable of reacting with an analyte in an aqueous fluid sample to produce a measurable change in potential which can be correlated to the concentration of the analyte in the fluid sample.

2. The process of claim 1 wherein step (c) further comprises forming a reference electrode comprising a third electrode having a third electrode area, a third lead and a third contact pad.

3. The process of claim 2 wherein the reference material is silver/silver chloride.

4. The process of claim 1 wherein step (c) further comprises the steps of:
   (e) applying a photoresist to the conductive layer to form a first photoresist layer;
   (f) positioning a first developer mask on the first photoresist layer;
   (g) exposing the unmasked first photoresist layer to ultraviolet light to form a first patterned photoresist area;
   (h) removing the first developer mask;
   (i) removing the first photoresist layer not exposed to ultraviolet light with a developer to form a first exposed conductive layer;
   (j) contacting the first exposed layer with a chemical etchant to remove the first exposed conductive layer;
   (k) removing the first patterned photoresist area with a solvent to form a second exposed conductive layer, said second exposed conductive area comprising (i) a working electrode comprising a first electrode having a first electrode area, a first lead and a first contact pad, (ii) a counter electrode comprising a second electrode having a second electrode area, a second lead and a second contact pad, and optionally (iii) a reference electrode comprising a third electrode having a third electrode area, a third lead and a third contact pad.

5. The process of claim 4 wherein step (c) above further comprises the steps of:
(l) applying a photoresist to the second exposed conductive layer to form a second photoresist layer;
(m) positioning a second developer mask on the second photoresist so that the second photoresist layer covering the third electrode area is masked;
(n) exposing the unmasked second photoresist layer to ultraviolet light to form a second patterned photoresist layer;
(o) removing the second developer mask;
(p) removing the second photoresist layer not exposed to ultraviolet light with a developer to expose the third electrode area;
(q) applying a reference material to the third electrode area;
(r) removing the second patterned photoresist layer with a solvent.

6. A process of claim 1 wherein said process is continuous.

7. The process of claim 1 wherein the flexible material is metallic.

8. The process of claim 1 wherein the flexible material is a polymeric sheet material.

9. The process of claim 8 wherein the polymeric sheet material is selected from the group consisting of polyesters, polycarbonates and polyimides.

10. The process of claim 1 wherein the non-conductive coating is an epoxy resin.

11. The process of claim 1 wherein the amorphous semiconductor material is amorphous silicon oxide.

12. The process of claim 11 wherein the amorphous silicon oxide is doped with an ion to increase conductivity.

13. The process of claim 12 wherein the amorphous silicon oxide is doped with lithium.

14. The process of claim 1 where the amorphous semiconductor material is gold.

15. The process of claim 1 where the amorphous semiconductor material is silver.

16. The process of claim 1 wherein the reagent comprises an enzyme and a redox mediator.

17. The process of claim 16 wherein the enzyme is glucose oxidase.

18. The process of claim 17 wherein the redox mediator is potassium ferricyanide.

19. The process of claim 1 wherein the electrochemical test device further comprises a blood separating membrane.

* * * * *